(12) United States Patent
Kim

(10) Patent No.: US 12,161,684 B1
(45) Date of Patent: Dec. 10, 2024

(54) METHOD OF PREPARING FERMENTED HERBAL EYE DROPS

(71) Applicant: Jihwan Kim, Seoul (KR)

(72) Inventor: Jihwan Kim, Seoul (KR)

( * ) Notice: Subject to any disclaimer, the term of this patent is extended or adjusted under 35 U.S.C. 154(b) by 0 days.

(21) Appl. No.: 18/636,644

(22) Filed: Apr. 16, 2024

(30) Foreign Application Priority Data

May 19, 2023 (KR) .................. 10-2023-0064694

(51) Int. Cl.
| | | |
|---|---|---|
| *A61K 36/815* | (2006.01) | |
| *A61K 36/07* | (2006.01) | |
| *A61K 36/074* | (2006.01) | |
| *A61K 36/185* | (2006.01) | |
| *A61K 36/258* | (2006.01) | |
| *A61K 36/28* | (2006.01) | |
| *A61K 36/33* | (2006.01) | |
| *A61K 36/45* | (2006.01) | |
| *A61K 36/481* | (2006.01) | |
| *A61K 36/484* | (2006.01) | |
| *A61K 36/60* | (2006.01) | |
| *A61K 36/605* | (2006.01) | |
| *A61K 36/725* | (2006.01) | |
| *A61K 36/752* | (2006.01) | |
| *A61K 36/804* | (2006.01) | |
| *A61K 36/8962* | (2006.01) | |
| *A61K 36/906* | (2006.01) | |

(52) U.S. Cl.
CPC ............ *A61K 36/258* (2013.01); *A61K 36/33* (2013.01); *A61K 36/45* (2013.01); *A61K 36/484* (2013.01); *A61K 36/605* (2013.01); *A61K 36/725* (2013.01); *A61K 36/8962* (2013.01); *A61K 36/906* (2013.01); *A61K 2236/19* (2013.01); *A61K 2236/39* (2013.01)

(58) Field of Classification Search
None
See application file for complete search history.

(56) References Cited

FOREIGN PATENT DOCUMENTS

| KR | 10-2012-0103918 A | | 9/2012 |
|---|---|---|---|
| KR | 20120103918 A | * | 5/2013 |
| KR | 10-1740869 B1 | | 5/2017 |
| KR | 10-1759697 B1 | * | 7/2017 |
| KR | 10-2002612 B1 | | 7/2019 |

OTHER PUBLICATIONS

Request for the Submission of an Opinion in Korean Application No. 10-2023-0064694 dated Jul. 11, 2023.
Written decision on registration for Korean Application No. 10-2023-0064694 dated Oct. 26, 2023.

* cited by examiner

*Primary Examiner* — Nghi V Nguyen
(74) *Attorney, Agent, or Firm* — Sughrue Mion, PLLC

(57) ABSTRACT

The present invention relates to a method of preparing fermented herbal eye drops, and the method includes an herbal medicine washing process of mixing an herbal medicine mixture, vinegar, and coarse salt in purified water, allowing it to stand, and then washing it; a heating process of inputting the herbal medicine mixture washed through the herbal medicine washing process into a decoction pot, mixing the herbal medicine mixture with purified water, and heating the herbal medicine mixture mixed with purified water; a cooling and fermentation process of cooling decoction prepared through the heating process and then fermenting the decoction; an eye drop raw material extraction process of distilling a fermented product prepared through the cooling and fermentation process to extract raw materials for eye drops; and an alkaline water mixing process of mixing alkaline water with the raw materials for eye drops prepared through the eye drop raw material extraction process. The fermented herbal eye drops prepared through the above process do not contain chemical components, have low cytotoxicity, are safe for the human body, and have an excellent sterilizing effect, thereby improving eye diseases such as inflammation or redness.

3 Claims, 2 Drawing Sheets

[Fig. 1]

METHOD OF PREPARING FERMENTED HERBAL EYE DROPS

CROSS-REFERENCE TO RELATED APPLICATION

This application claims priority to and the benefit of Korean Patent Application No. 2023-0064694, filed on May 19, 2023, the disclosure of which is incorporated herein by reference in its entirety.

BACKGROUND

1. Field of the Invention

The present invention relates to a method of preparing fermented herbal eye drops, and more specifically, to a method of preparing fermented herbal eye drops that do not contain chemical components, have low cytotoxicity, are safe for the human body, and have an excellent sterilizing effect, thereby improving eye diseases such as inflammation or redness.

2. Discussion of Related Art

Modern people suffer from eye diseases caused by excessive energy and blood consumption in the eyes due to the use of numerous electronic devices. In particular, excessive use of smartphones and computers causes chronic diseases such as dry eye, and an increasing number of people are using eye drops to improve them.

Additionally, excessive stress can cause blood circulation problems around the eye and in the eye itself, causing inflammation or damage to retinal cells, leading to incurable eye diseases such as glaucoma or macular degeneration, and in the worst case, leading to blindness.

There are more than a thousand types of eye drops used for dry eye around the world, but most of them are made using synthetic chemicals or chemicals, and eye drops using these chemicals may help with short-term symptoms, but their effect on improving blood flow in the eye itself or treating the conjunctiva or retina is minimal.

In this situation, for the development and clinical application of eye drops made from natural herbal medicines, attempts are being made to develop eye drops using safe herbal medicines whose safety has been clinically confirmed over thousands of years based on the basic principles of oriental medicine.

RELATED ART DOCUMENTS

Patent Documents (Patent Document 1) Korean Patent Registration No. 10-1740869 (May 22, 2017)
(Patent Document 2) Korean Patent Registration No. 10-2002612 (Jul. 16, 2019)

SUMMARY OF THE INVENTION

The present invention is directed to providing a method of preparing fermented herbal eye drops that do not contain chemical components, have low cytotoxicity, are safe for the human body, and have an excellent sterilizing effect, thereby improving eye diseases such as inflammation or redness.

The purpose of the present invention is to provide a method of preparing fermented herbal eye drops, including: an herbal medicine washing process of mixing an herbal medicine mixture, vinegar, and coarse salt in purified water, allowing it to stand, and then washing it; a heating process of inputting the herbal medicine mixture washed through the herbal medicine washing process into a decoction pot, mixing the herbal medicine mixture with purified water, and heating the herbal medicine mixture mixed with purified water; a cooling and fermentation process of cooling decoction prepared through the heating process and then fermenting the decoction; an eye drop raw material extraction process of distilling a fermented product prepared through the cooling and fermentation process to extract raw materials for eye drops; and an alkaline water mixing process of mixing alkaline water with the raw materials for eye drops prepared through the eye drop raw material extraction process, wherein the herbal medicine mixture includes equal amounts of wolfberry, rhemannia, shiitake mushrooms, reishi mushrooms, mulberry leaves, mulberry roots, deer antler, ginseng, *Astragalus membranaceus* Bunge, *Fraxinus rhynchophylla* Hance, *Chrysanthemum indicum, taraxacum, Tribulus terrestris*, cuscuta seeds, onion, *portulaca*, eastern prickly pear, ginger, jujube, and licorice.

According to a preferred feature of the present invention, in the herbal medicine washing process, 10 to 15 parts by weight of herbal medicine mixture, 1 to 2 parts by weight of vinegar, and 0.2 to 0.4 parts by weight of coarse salt are mixed in 100 parts by weight of purified water and allowed to stand for 4 to 6 minutes, and then the herbal medicine mixture is washed.

According to a preferred feature of the present invention, in the heating process, 400 to 600 parts by weight of purified water is mixed based on 100 parts by weight of the herbal medicine mixture washed through the herbal medicine washing process, heated at a temperature of 100 to 120° C. for 8 to 10 hours, and then heated at a temperature of 80 to 90° C. for 10 to 15 hours.

According to a preferred feature of the present invention, the decoction prepared through the heating process is cooled to a temperature of 40 to 45° C., and then 0.01 to 0.1 parts by weight of a fermentation strain is inoculated into 100 parts by weight of the cooled decoction and fermented for 14 to 16 hours.

According to a preferred feature of the present invention, the fermentation strain is a mixture of *Lactobacillus acidophilus, Lactobacillus bulgaricus, Lacticaseibacillus paracasei, Bifidobacterium breve*, and *Lacticaseibacillus rhamnosus* in a weight ratio of 1:1:1:1:1.

According to a preferred feature of the present invention, the alkaline water mixing process is performed by mixing 0.05 to 0.15 parts by weight of the raw materials for eyes drops prepared through the eye drop raw material extraction with 100 parts by weight of alkaline water.

According to a preferred feature of the present invention, the alkaline water has a pH of 7.2 to 7.6.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
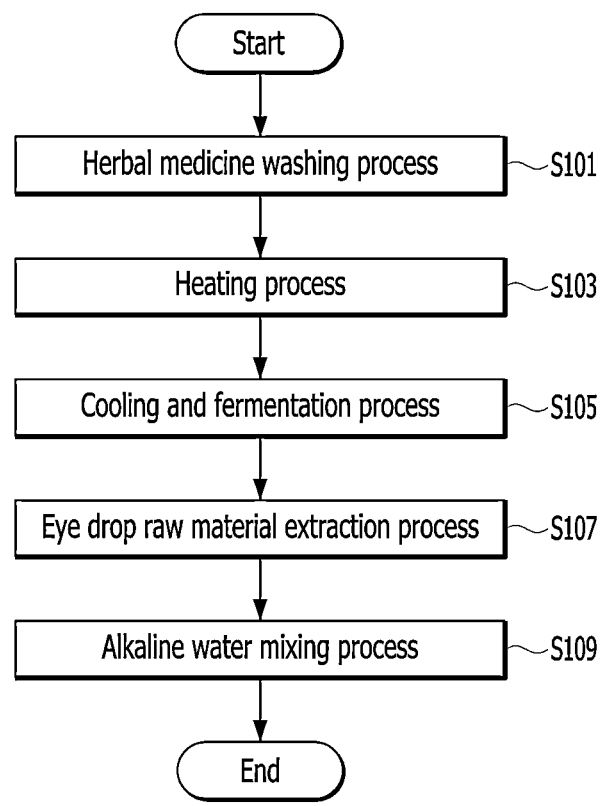
FIG. 1 is a flow chart showing a method of preparing fermented herbal eye drops according to the present invention.

Hereinafter, preferred embodiments of the present invention and the physical properties of each component are described in detail, but this is intended to provide a description in enough detail that a person with ordinary knowledge in the art to which the present invention belongs can easily practice the invention, and is not meant to limit the technical spirit and scope of the present invention.

A method of preparing fermented herbal eye drops according to the present invention includes an herbal medicine washing process (S101) of mixing an herbal medicine mixture, vinegar, and coarse salt in purified water, allowing it to stand, and then washing it; a heating process (S103) of inputting the herbal medicine mixture washed through the herbal medicine washing process into a decoction pot, mixing the herbal medicine mixture with purified water, and heating the herbal medicine mixture mixed with purified water; a cooling and fermentation process (S105) of cooling the decoction prepared through the heating process (S103) and then fermenting the decoction; an eye drop raw material extraction process (S107) of distilling a fermented product prepared through the cooling and fermentation process (S105) to extract raw materials for eye drops; and an alkaline water mixing process (S109) of mixing alkaline water with the raw materials for eye drops prepared through the eye drop raw material extraction process (S107).

The herbal medicine washing process (S101) is a step of mixing an herbal medicine mixture, vinegar, and coarse salt in purified water, allowing it to stand, and then washing it, and it is preferable that 10 to 15 parts by weight of herbal medicine mixture, 1 to 2 parts by weight of vinegar, and 0.2 to 0.4 parts by weight of coarse salt are mixed in 100 parts by weight of purified water and allowed to stand for 4 to 6 minutes, and then the herbal medicine mixture is separated from the mixture, and the separated herbal medicine mixture is washed by rubbing against each other.

Through the above process, foreign matter remaining on the surface of the herbal medicine is removed, and at this time, preferably, the herbal medicine mixture includes wolfberry, rhemannia, shiitake mushrooms, reishi mushrooms, mulberry leaves, mulberry roots, deer antler, *ginseng*, *Astragalus membranaceus* Bunge, *Fraxinus rhynchophylla* Hance, *Chrysanthemum indicum*, *taraxacum*, *Tribulus terrestris*, cuscuta seeds, onion, *portulaca*, eastern prickly pear, ginger, jujube, and licorice, and more preferably, equal parts by weight of wolfberry, rhemannia, shiitake mushrooms, reishi mushrooms, mulberry leaves, mulberry root, deer antler, *ginseng*, *Astragalus membranaceus* Bunge, *Fraxinus rhynchophylla* Hance, *Chrysanthemum indicum*, *taraxacum*, *Tribulus terrestris*, cuscuta seeds, onion, *portulaca*, eastern prickly pear, ginger, jujube, and licorice.

The leaves and fruits of the mulberry, shiitake mushrooms, and reishi mushrooms serve to provide nutrients necessary for the eyes.

In addition, the wolfberry and rehmannia not only serve to provide nutrients needed for the eyes, but also function to restore damaged eye cells and repair conjunctival and retinal cells damaged due to excessive use of the eyes, thereby improving diseases such as dry eye and macular degeneration.

In addition, the above-mentioned *Tribulus terrestris*, *taraxacum*, and *Chrysanthemum indicum* play a role in improving conjunctivitis or optic neuritis caused by inflammation due to impaired blood flow in the eye.

In addition, the deer antler, *ginseng*, *Astragalus membranaceus* Bunge, and *Fraxinus rhynchophylla* Hance improve the circulation of energy and blood, and the onion and *portulaca* play a role in improving eye redness by removing stagnant blood.

The heating process (S103) is a step of inputting the herbal medicine mixture washed through the herbal medicine washing process (S101) into a decoction pot, mixing the herbal medicine mixture with purified water, and heating the herbal medicine mixture mixed with purified water, and it is preferable that 100 parts by weight of the herbal medicine mixture washed through the herbal medicine washing process (S101) is input into a decoction pot, mixed with 400 to 600 parts by weight of purified water, heated at a temperature of 100 to 120° C. for 8 to 10 hours, and then heated at a temperature of 80 to 90° C. for 10 to 15 hours.

When the content of purified water in the heating process (S103) is less than 400 parts by weight, the purified water decreases too much during the heating process, preventing proper extraction of the active ingredients contained in the herbal medicine mixture, and when the content of purified water exceeds 600 parts by weight in the heating step (S103), it is undesirable because the concentration of the prepared decoction is too low and a separate concentration process needs to be performed.

In addition, when the initial heating temperature of the heating process (S103) is less than 100° C. or the heating time is less than 8 hours, the above effect is minimal, and when the initial heating temperature of the heating exceeds 120° C. or the heating time exceeds 10 hours, the elution effect of the active ingredients contained in the herbal medicine mixture is not significantly improved and the extracted active ingredients are destroyed, which is undesirable in terms of energy efficiency.

The cooling and fermentation process (S105) is a step of cooling the decoction prepared through the heating process (S103) and then fermenting the decoction, and it is preferable that the decoction prepared through the heating process (S103) is cooled to a temperature of 40 to 45° C. and then 0.01 to 0.1 parts by weight of the fermentation strain is inoculated into 100 parts by weight of the cooled decoction and fermented for 14 to 16 hours.

When the fermentation process is performed as described above, the active components extracted from the herbal medicine mixture are refined into small nano-sized particles, greatly improving the absorption rate in the body.

At this time, it is preferable that the fermentation strain is a mixture of *Lactobacillus acidophilus*, *Lactobacillus bulgaricus*, *Lacticaseibacillus paracasei*, *Bifidobacterium breve*, and *Lacticaseibacillus rhamnosus* in a weight ratio of 1:1:1:1:1 because fermentation strains composed of the above strains help each other in the necessary areas to ferment natural medicines, thereby increasing the fermentation efficacy of natural medicines used in the preparation of eye drops.

When the temperature of the cooling and fermentation process (S105) is less than 40° C. or the fermentation time is less than 14 hours, the efficiency of the fermentation process is low and the above effect is minimal, and when the temperature of the cooling and fermentation process (S105) exceeds 45° C. or the fermentation time exceeds 16 hours, it is undesirable because anaerobic fermentation may proceed without significantly improving the above effect.

The eye drop raw material extraction process (S107) is a step of distilling a fermented product prepared through the cooling and fermentation process (S105) to extract raw materials for eye drops, and the extraction process includes putting the fermented product prepared through the cooling and fermentation process (S105) into a distillation device and extracting it by distillation, wherein the conditions for distillation extraction in the eye drop raw material extraction process (S107) performed in the present invention may be performed by applying the conditions for conventional distillation extraction.

Figure 2:
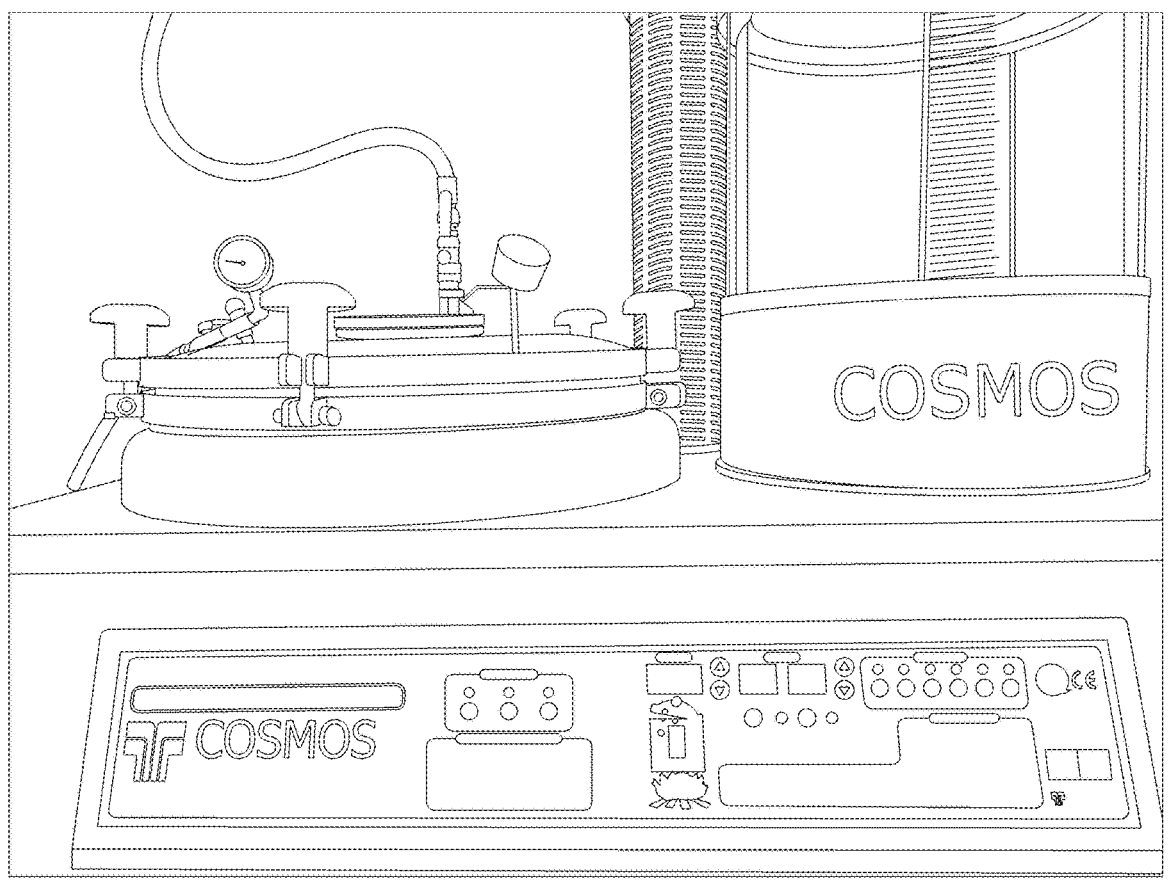
FIG. 2 is a photograph showing a distillation extraction device used in the present invention.

In addition, as long as the distillation extraction device used in the eye drop raw material extraction process (S107) of the present invention is capable of distilling and extracting the eye drop active ingredient contained in the fermentation product prepared through the cooling and fermentation process (S105) as described above, there is no particular limitation and any device can be used, but it is preferable to use the distillation extraction device shown in FIG. 2.

The alkaline water mixing process (S109) is a step of mixing alkaline water with the raw materials for eye drops prepared through the eye drop raw material extraction process (S107), and it is preferable to mix 0.05 to 0.15 parts by weight of the raw materials for eye drops prepared through the eye drop raw material extraction process (S107) with 100 parts by weight of alkaline water.

At this time, it is preferable to use alkaline water having a pH of 7.2 to 7.6, and the alkaline water used in the present invention may be prepared using the "electrolytic water purifier" described in Korean Patent Registration No. 10-0419536.

Eye drops using alkaline water prepared through an electrolytic water purifier as described above have a pH similar to tears, making it comfortable for the eyes and preventing rejection. When the pH of the alkaline water is less than 7.2, it is undesirable because the pH is too low compared to tears, and when the pH of the alkaline water exceeds 7.6, the pH of the prepared eye drops is too high, which is undesirable because irritation to the eyes may increase.

In addition, when the content of the raw materials for eye drops mixed in the alkaline water mixing process (S109) is less than 0.05 parts by weight, the sterilization effect is too low and the effect of suppressing eye diseases early or improving eye diseases such as inflammation or redness is minimal, and when the content of the raw materials for eye drops exceeds 0.15 parts by weight, it is undesirable because cytotoxicity or eye irritation may excessively increase without significantly improving the above effects.

After going through the alkaline water mixing process (S109), the preparation of the fermented herbal eye drops according to the present invention is completed, and the fermented herbal eye drops prepared through the present invention may contain one or more components selected from anti-inflammatory agents (allantoin, pranoprofen, and the like), antiphlogistics (naphazoline hydrochloride, and the like), ocular regulators (neostigmine methyl sulfate, and the like), astringents (zinc sulfate, and the like), antihistamines (chlorpheniramine maleate, diphenylhydramine hydrochloride, and the like), anti-allergic agents (sodium cromoglycate, and the like), vitamins (tocopherol acetate, flavin adenine dinucleotide sodium, pyridoxine hydrochloride, cyanocobalamin, panthenol, and the like), sulfa drugs (sulfamethoxazole, and the like), sodium chondroitin sulfate, amino acids, and the like within a range that does not affect the intended purpose and effect.

In addition, the fermented herbal eye drops prepared through the present invention are particularly suitable for eye drops and eye ointments among dosage forms including eye drops, eye ointments, powders, granules, tablets, capsules, injections, and the like, and preparations of these dosage forms may be prepared by conventional methods.

Aqueous solutions and diluents for suspensions used in the above eye drops include distilled water and physiological saline, and non-aqueous solutions and diluents for suspensions include vegetable oil, liquid paraffin, mineral oil, propylene glycol, and p-octyldodecanol.

In addition, the eye drop composition of the present invention may be used for the prevention or treatment of the above diseases or symptoms in humans and non-human animals [for example, mammals other than humans (livestock and pets such as pigs, cows, horses, dogs, cats, and the like)].

Hereinafter, the method of preparing the fermented herbal eye drops according to the present invention and the physical properties of the fermented herbal eye drops prepared by the method will be described using examples.

<Preparation Example 1> Preparation of Herbal Medicine Mixture 40 g of wolfberry, 40 g of rhemannia, 40 g of shiitake mushrooms, 40 g of reishi mushrooms, 40 g of mulberry leaves, 40 g of mulberry root, 40 g of deer antler, 40 g of ginseng, 40 g of *Astragalus membranaceus* Bunge, 40 g of *Fraxinus rhynchophylla* Hance, 40 g of *Chrysanthemum indicum*, 40 g of *taraxacum*, 40 g of *Tribulus terrestris*, 40 g of cuscuta seeds, 40 g of onion, 40 g of *portulaca*, 40 g of eastern prickly pear, 40 g of ginger, 40 g of jujube, and 40 g of licorice were mixed to prepare 800 g of an herbal medicine mixture.

<Preparation Example 2> Preparation of Fermentation Strain

*Lactobacillus acidophilus*, *Lactobacillus bulgaricus*, *Lacticaseibacillus paracasei*, *Bifidobacterium breve*, and *Lacticaseibacillus rhamnosus* were mixed in a weight ratio of 1:1:1:1:1 to prepare a fermentation strain.

Example 1

Fermented herbal eye drops were prepared as follows:

After 800 g of the herbal medicine mixture prepared through Preparation Example 1, 90 mL of vinegar, and 20 g of coarse salt were mixed in 6 L of purified water and allowed to stand for 5 minutes, the herbal medicine mixture was separated, rubbed, and washed by rinsing three times, and then the washed herbal medicine mixture was put into a non-woven bag for decoction, which was then put into a decoction pot, 2 L of purified water was added into the decoction pot and heated at a temperature of 110° C. for 9 hours and then further heated at a temperature of 85° C. for 12 hours to extract a decoction, the extracted decoction was cooled to a temperature of 42° C., and then 0.05 parts by weight of the fermentation strain (based on 100 parts by weight of the cooled decoction) prepared through Preparation Example 2 above was mixed and fermented for 15 hours, the fermented broth was input into a distillation extractor and extracted by distillation to prepare raw materials for eye drops, and 100 parts by weight of alkaline water (pH 7.4) was mixed with 0.1 parts by weight of the prepared raw materials for eye drops.

Example 2

The procedure was the same as in Example 1, but 0.05 parts by weight of the raw materials for eye drops were mixed to prepare fermented herbal eye drops.

Example 3

The procedure was the same as in Example 1, but 0.15 parts by weight of the raw materials for eye drops were mixed to prepare fermented herbal eye drops.

Comparative Example 1

Fermented herbal eye drops were prepared as follows:
After 800 g of the herbal medicine mixture prepared through Preparation Example 1, 90 mL of vinegar, and 20 g of coarse salt were mixed in 6 L of purified water and allowed to stand for 5 minutes, the herbal medicine mixture was separated, rubbed, and washed by rinsing three times, and then the washed herbal medicine mixture was put into a non-woven bag for decoction, which was then put into a decoction pot, 2 L of purified water was added into the decoction pot and heated at a temperature of 110° C. for 9 hours and then further heated at a temperature of 85° C. for 12 hours to extract a decoction, the extracted decoction was cooled to a temperature of 42° C., and then the cooled decoction was input into a distillation extractor and extracted by distillation to prepare raw materials for eye drops, and 100 parts by weight of alkaline water (pH 7.4) was mixed with 0.1 parts by weight of the raw materials for eye drops.

Comparative Example 2

The procedure was the same as in Example 1, but 0.01 parts by weight of the raw materials for eye drops were mixed to prepare eye drops.

Comparative Example 3

The procedure was the same as in Example 1, but 1.0 parts by weight of the raw materials for eye drops were mixed to prepare eye drops.

The eye inflammation and eye redness improvement effects of the eye drops prepared through Examples 1 to 3 and Comparative Examples 1 to 3 were measured and are shown in Table 1 below.

Here, the effects of improving eye inflammation and eye redness target 60 subjects with eye inflammation and 60 subjects with eye redness, wherein, after grouping 10 people into 6 groups, the prepared eyedrops were administered to each group at 0.45 mL three times a day at 6-hour intervals for 2 days, and the effects of improving eye inflammation and eye redness were evaluated using a 5-point scale and expressed as average values.

5 points: very improved, 4 points: improved, 3 points: moderate, 2 points: worsened, 1 point: very worsened.

TABLE 1

| Classification | Eye inflammation | Eye redness |
| --- | --- | --- |
| Example 1 | 4.5 | 4.4 |
| Example 2 | 4.2 | 4.3 |
| Example 3 | 4.6 | 4.5 |

TABLE 1-continued

| Classification | Eye inflammation | Eye redness |
| --- | --- | --- |
| Comparative Example 1 | 4.0 | 3.9 |
| Comparative Example 2 | 3.4 | 3.2 |
| Comparative Example 3 | 4.6 | 4.4 |

As shown in Table 1, it can be seen that the eye drops prepared in Examples 1 to 3 of the present invention have an excellent effect in improving eye inflammation and eye redness compared to the eye drops prepared in Comparative Examples 1 to 2. In particular, it can be seen that even when the same components are mixed, the eye inflammation and eye redness improvement effects are reduced in Comparative Example 1 in which the fermentation process does not proceed.

In addition, it can be seen that even when excessive amounts of raw materials for eye drops are used as in Comparative Example 3, the eye inflammation and eye redness improvement effects are not significantly improved.

In addition, the cytotoxicity of the eye drops prepared through Examples 1 to 3 and Comparative Examples 1 to 3 was tested and the results are shown in Table 2 below.

Here, for the cytotoxicity test, RAW 264.7 cells, a mouse macrophage cell line, were purchased from the Korea Cell Line Bank (KCLB) and cultured in an incubator controlled at 37° C. and 4% $CO_2$ using an RPMI 1640 medium containing 10% fetal bovine serum (FBS), 1% antibiotics, and 2-mercaptoethanol (2-ME).

The cultured mouse macrophage cell line RAW2647 was dispensed into a 96-well plate at $5 \times 10^4$ cells/100 μl per well and then cultured in $CO_2$ for 24 hours. One hour after treatment with lipopolysaccharide (LPS) at a concentration of 1 μg/ml, the cells were treated with the eye drops of Examples 1 to 3 and Comparative Examples 1 to 3 and cultured in $CO_2$ for 24 hours. Next, 100 μl of each culture supernatant was removed, 10 μl of CCK-8 reagent was treated, cultured in $CO_2$ for 3 hours, and then absorbance was measured at 450 nm using a microplate reader.

TABLE 2

| Classification | Cell viability |
| --- | --- |
| Control | 100.00 ± 0.2 |
| LPS | 97.64 ± 0.9 |
| Example 1 | 99.77 ± 0.3 |
| Example 2 | 99.80 ± 0.4 |
| Example 3 | 99.74 ± 0.3 |
| Comparative Example 1 | 98.90 ± 0.5 |
| Comparative Example 2 | 99.91 ± 0.2 |
| Comparative Example 3 | 97.58 ± 0.6 |

As shown in Table 2, it can be seen that the fermented herbal eye drops prepared through Examples 1 to 3 of the present invention have very low cytotoxicity. On the other hand, it can be seen that the eye drops prepared through Comparative Example 3 had relatively increased cytotoxicity.

Therefore, the method of preparing fermented herbal eye drops according to the present invention provides fermented herbal eye drops that do not contain chemical components, have low cytotoxicity, are safe for the human body, and have an excellent sterilizing effect, thereby improving eye diseases such as inflammation or redness.

In addition, the fermented herbal eye drops according to the present invention can show the effects of improving eye diseases such as dry eye and improving intraocular pressure control through the energy and blood circulation and blood replenishing actions of herbal medicine.

A method of preparing fermented herbal eye drops according to the present invention can provide fermented herbal eye drops that do not contain chemical components, have low cytotoxicity, are safe for the human body, and have an excellent sterilizing effect, thereby improving eye diseases such as inflammation or redness.

What is claimed is:

1. A method of preparing fermented herbal eye drops, comprising:
    an herbal medicine washing process of mixing an herbal medicine mixture, vinegar, and coarse salt in purified water, allowing it to stand, and then washing it;
    a heating process of inputting the herbal medicine mixture washed through the herbal medicine washing process into a decoction pot, mixing the herbal medicine mixture with purified water, and heating the herbal medicine mixture mixed with purified water;
    a cooling and fermentation process of cooling decoction prepared through the heating process and then fermenting the decoction;
    an eye drop raw material extraction process of distilling a fermented product prepared through the cooling and fermentation process to extract raw materials for eye drops; and
    an alkaline water mixing process of mixing alkaline water with the raw materials for eye drops prepared through the eye drop raw material extraction process,
    wherein the herbal medicine mixture includes equal amounts of wolfberry, rhemannia, shiitake mushrooms, reishi mushrooms, mulberry leaves, mulberry roots, deer antler, ginseng, *Astragalus membranaceus* Bunge, *Fraxinus rhynchophylla* Hance, *Chrysanthemum indicum, taraxacum, Tribulus terrestris*, cuscuta seeds, onion, *portulaca*, eastern prickly pear, ginger, jujube, and licorice,
    in the cooling and fermentation process, the decoction prepared through the heating process is cooled to a temperature of 40 to 45° C., and then 0.01 to 0.1 parts by weight of a fermentation strain is inoculated into 100 parts by weight of the cooled decoction and fermented for 14 to 16 hours,
    the fermentation strain is a mixture of *Lactobacillus acidophilus, Lactobacillus bulgaricus, Lacticaseibacillus paracasei, Bifidobacterium breve*, and *Lacticaseibacillus rhamnosus* in a weight ratio of 1:1:1:1:1,
    the alkaline water mixing process is performed by mixing 0.05 to 0.15 parts by weight of the raw materials for eyes drops prepared through the eye drop raw material extraction process with 100 parts by weight of alkaline water, and
    the alkaline water has a pH of 7.2 to 7.6.

2. The method of claim 1, wherein, in the herbal medicine washing process, 10 to 15 parts by weight of herbal medicine mixture, 1 to 2 parts by weight of vinegar, and 0.2 to 0.4 parts by weight of coarse salt are mixed in 100 parts by weight of purified water and allowed to stand for 4 to 6 minutes, and then the herbal medicine mixture is washed.

3. The method of claim 1, wherein, in the heating process, 400 to 600 parts by weight of purified water is mixed based on 100 parts by weight of the herbal medicine mixture washed through the herbal medicine washing process, heated at a temperature of 100 to 120° C. for 8 to 10 hours, and then heated at a temperature of 80 to 90° C. for 10 to 15 hours.

* * * * *